(12) United States Patent
Van Der Schaaf et al.

(10) Patent No.: US 6,407,190 B1
(45) Date of Patent: Jun. 18, 2002

(54) RUTHENIUM AND OSMIUM CARBENE CATALYSTS

(75) Inventors: Paul Adriaan Van Der Schaaf, Allschwil; Andreas Hafner, Gelterkinden; Andreas Mühlebach, Frick, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/445,909

(22) PCT Filed: Jun. 13, 1998

(86) PCT No.: PCT/EP98/03573

§ 371 (c)(1),
(2), (4) Date: Dec. 15, 1999

(87) PCT Pub. No.: WO99/00396

PCT Pub. Date: Jan. 7, 1999

(30) Foreign Application Priority Data

Jun. 25, 1997 (CH) .............................................. 1536/97

(51) Int. Cl.[7] .................................................. C08F 4/80
(52) U.S. Cl. ........................ 526/171; 556/13; 556/136; 526/308
(58) Field of Search ................................ 526/171, 308; 556/13, 136

(56) References Cited

FOREIGN PATENT DOCUMENTS

WO 93/20111 10/1993

OTHER PUBLICATIONS

Wu et al., "Reactions of Ruthenium Carbenes of the Type (PPh3)2 (X)2 Ru=CH–CH=CPh2 (X=C and CF3COO) with Strained Acyclic Olefins and Functionalized Olefins", J. Am. Chem. Soc. 1995, vol. 117, p. 5503–5511.*

A. Hartshorn et al., J. Chem. Soc., Dalton Trans., (1978), (4), pp. 348–356.*

Z. Wu et al., J. Am. Chem. Soc. 1995, vol. 117, No. 20, pp. 5503–5511.

A. Hartshorn et al., J. Chem. Soc., Dalton Trans., (1978), (4), pp. 348–356.

D. Christian et al., Journal of Organometallic Chemistry, vol. 81, (1974), C7–C8.

D. Christian et al., Journal of Organometallic Chemistry, vol. 80, (1974), C35–C38.

* cited by examiner

Primary Examiner—David W. Wu
Assistant Examiner—William K Cheung
(74) Attorney, Agent, or Firm—Kevin T. Mansfield

(57) ABSTRACT

The invention relates to penta- and hexacoordinated ruthenium and osmium carbene catalysts, in which a sulfur, oxygen or nitrogen atom is attached to the carbene group which is coordinated with the central ruthenium or osmium atom, to their preparation and to their use for synthesizing polymers, for ring-closing metathesis of olefins and for isomerizing olefins.

10 Claims, No Drawings

RUTHENIUM AND OSMIUM CARBENE CATALYSTS

The invention relates to penta- and hexacoordinated ruthenium and osmium carbene catalyst, to their preparation and to their use for synthesizing polymers, for ring-closing metathesis of olefins and for isomerizing olefins.

The thermal metathesis polymerization of cycloolefins which are under ring strain, which has acquired great importance in recent times, requires appropriate catalysts. Whereas initially use was made of catalyst and cocatalyst—see, for example U.S. Pat. No. 4,060,468 and International Patent Application WO 93/13171—one-component catalysts have also been disclosed [H. H. Thai et al., *J. Mol. Catal.* 15:245–270 (1982)]. Catalysts of particular interest for the application are so-called metal carbenes, i.e. transition metal compounds, for example ruthenium and osmium complexes, having a group =CR'R'' attached to the central metal atom [WO 93/201111; S. Kanaoke et al., *Macromolecules* 28:4707–4713 (1995); C. Fraser et al., *Polym. Prepr.* 36:237–238 (1995); P. Schwab et al., *Angew. Chem.* 107:2179–2181 (1995)]. This type of complex is also suitable for catalysing ring closure in dienes [WO 96/04289]. The known catalysts are pentacoordinated and in addition to the group =CR'R'' contain two identical tertiary phosphine groups, attached to the metal atoms, as neutral e⁻ donor ligands [WO 93/20111; WO 96/04289]. Z. Wu et al., J. Amer. Chem. Soc. 1995, 117, 5503–5511 disclose on page 5 the alkanethio-substituted ruthenium carbene complex (trifluoroacetate)$_2$(PPh$_3$)$_2$Ru(CHSCH$_2$Ph). However, it is also disclosed on page 5508, left column, last sentence, that this complex is inactive for catalyzing the ROMP (=Ring Opening Metathesis Polymerization) of bicyclo[3.2.0]hept-6-ene.

The present invention is based on the object of providing further. improved catalysts for thermal metathesis polymerization. It has surprisingly been found that pentacoordinated ruthenium and osmium catalysts having a group =CR'R'' (R'=hydrogen and R''=arylthio) attached to the central metal atom, and hexacoordinated ruthenium and osmium catalysts having the group =CR'R'' in which one of the radicals R' or R'' is an organic radical which is attached via a nonmetallic heteroatom of the oxygen, sulfur or nitrogen type to the carbon atom of the carbene group, are excellent catalysts for metathesis reactions and for the ring closure of dienes. By an appropriate choice of neutral and anionic ligands it is possible to exercise close control over the reactivity, for example the latency, over a wide range.

The invention provides compounds of the formula

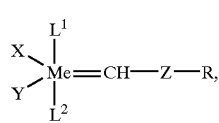
(Ia)

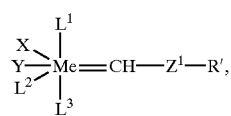
(Ib)

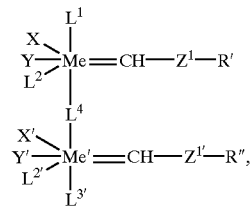
(Ic)

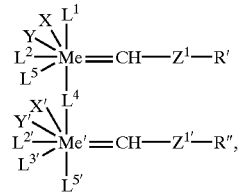
(Id)

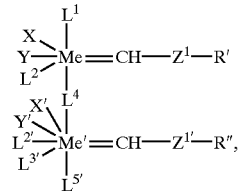
(Ie)

in which Me and Me' independently of one another are ruthenium or osmium;

X X', Y and Y' independently of one another are anionic ligands or X and Y and X' and Y' in each case together are bisanionic ligands;

L$^1$, L$^2$, L$^{2'}$, L$^3$, L$^{3'}$, L$^5$ and L$^{5'}$ independently of one another are monodentate, neutral e⁻ donor ligands;

L$^4$ is a bidentate- or, together with two of the ligands L$^1$, L$^2$, L$^{2'}$, L$^3$, L$^{3'}$, L$^5$ and L$^{5'}$, a tetradentate-neutral e⁻ donor ligand;

Z is sulfur or the group

(A')

in which R''' is hydrogen or a hydrocarbon radical;

Z$^1$ and Z$^{1'}$ independently of one another are oxygen, sulfur or the groups

(A)

and A';

R is unsubstituted or substituted arts if Z is sulfur or is a hydrocarbon radical if Z is the groups A and A'; and R' and R'' are a hydrocarbon radical, or an isomer of this compound;

with the exception of compounds (Ib), wherein one of L$^1$, L$^2$ and L$^3$ represents carbonyl.

The invention likewise provides compounds of the formulae Ia–Ie including all cases of isomerism of the type, for example, of coordination isomerism or bond isomerism, which results from differing spatial arrangement of the ligands around the central atom, but also stereoisomers. For compounds of the formula Ia the following isomeric structures of the formulae

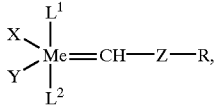 (Ia')

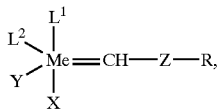 (Ia")

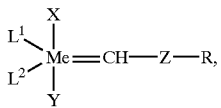 (Ia''')

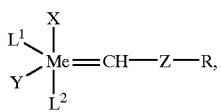 (Ia'''')

are possible, in which Me, X, Y, $L^1$, $L^2$, Z and R are as defined above. For compounds of the formulae Ib–Ie analogous isomeric structures are possible, which are likewise provided by the present invention. The invention likewise provides stereoisomeric compounds which result from the presence of a centre of chirality in one of the specified ligands or in a side chain. These cases of isomerism include optically pure enantiomners, diastereomers and racemic mixtures.

The terms and definitions used in the description of the present invention preferably have the following meanings:

In the compounds of the formula Ia–Ie Me and Me' are preferably ruthenium

The anionic ligands X, X', Y and Y' are, for example, hydride ions ($H^-$) or are derived from inorganic or organic acids, examples being halides, e.g. $F^-$, $Cl^-$, $Br^-$ or $I^-$, fluoro complexes of the type $BF_4^-$, $PF_6^-$, $SbFd_6^-$ or $AsF_6^-$, anions of oxygen acids, alcoholates or acetylides or anions of cyclopentadlene.

The anions of oxygen acids can be, for example, sulfate, phosphate, perchlorate, perbromate, periodate, antimonata, arsenate, nitrate, carbonate, the anion of a $C_1$–$C_8$carboxylic acid, such as formate, acetate, propionate, butyrate, benzoate, phenylacetate, mono-, di- or trichloro- or -fluoroacetate, sulfonates, for example methylsulfonate, ethylsulfonate, propylsulfonate, butylsulfonate, trifluoromethylsulfonate (triflate), unsubstituted or $C_1$–$C_4$alkyl, $C_1$–$C_4$alkoxy or halo-, especially fluoro-, chloro- or bromo-substituted phenylsulfonate or benzylsulfonate, for example tosylate, mesylate, brosylate, p-methoxy- or p-ethoxyphenylsulfonate, pentafluorophenylsulfonate or 2,4,6-triisopropylsulfonate.

Such anions are, for example, anions of oxygen acids, examples being sulfate, phosphate, perchlorate, perbromate, periodate, antimonate, arsenate, nitrate or carbonate, sulfonates, for example methylsulfonate, ethylsulfonate, propylsulfonate, butylsulfonate, trifluoromethylsulfonate (triflate), unsubstituted or $C_1$–$C_4$alkyl-, $C_1$–$C_4$alkoxy- or halo-, especially fluoro-, chloro- or bromo-substituted phenylsulfonate or benzylsulfonate, for example tosylate, mesylate, brosylate, p-methoxy- or p-ethoxyphenylsulfonate, pentafluorophenylsulfonate or 2,4,6-triisopropylsulfonate, phosphonates, for example methylphosphonate, ethylphosphonate, propylphosphonate, butylphosphonate, phenylphosphonate, p-methyl-phenylphosphonate or benzylphosphonate, carboxylates derived from a $C_1$–$C_8$carboxylic acid, for example formate, acetate, propionate, butyrate, benzoate, phenylacetate, mono-, di- or trichloro- or -fluoroacetate, and also $C_1$–$C_{12}$—, preferably $C_1$–$C_6$— and, with particular preference, $C_1$–$C_4$alcoholates, which in particular are branched, being for example of the formula $R_xR_yR_zC$—$O^-$ in which $R_x$ is H or $C_1$–$C_{10}$alkyl, $R_y$ is $C_1$–$C_{10}$alkyl and $R_z$ is $C_1$–$C_{10}$alkyl or phenyl, and the sum of the carbon atoms of $R_x$, $R_y$ and $R_z$ is at least 2, preferably at least 3 and up to 10.

Other suitable anions are $C_1$–$C_{12}$—, preferably $C_1$–$C_6$— and, with particular preference, $C_1$–$C_4$alcoholates, which in particular are branched, being for example of the formula $R_xR_yR_zC$—$O^-$ in which $R_x$ is H or $C_1$–$C_{10}$alkyl, $R_y$ is $C_1$–$C_{10}$alkyl and $R_z$ is $C_1$–$C_{10}$alkyl or phenyl, and the sum of the carbon atoms of $R_x$, $R_y$ and $R_z$ is at least 2, preferably at least 3 and up to 10.

Other suitable anions are $C_3$–$C_{18}$—, preferably $C_5$–$C_{14}$— and, with particular preference, $C_5$–$C_{12}$acetylides, which may be of the formula $R_w$—C≡$C^-$ in which $R_w$ is $C_1$–$C_{16}$alkyl, preferably α-branched $C_3$–$C_{12}$alkyl, for example of the formula $R_xR_yR_zC$—, or is unsubstituted or mono- to tri-$C_1$–$C_4$alkyl or —$C_1$–$C_4$alkoxy-substituted phenyl or benzyl. Some examples are i-propyl, i- and t-butyl, phenyl, benzyl, 2-methylphenyl, 2,6-dimethylphenyl, 2-i-propylphenyl, 2-i-propyl-6-methylphenyl, 2-t-butylphenyl, 2,6-di-t-butylphenyl and 2-methyl-6t-butylphenyl acetylide.

Further anionic ligands are organic radicals having negative charges, such as $C_1$–$C_{12}$alkyl, e.g. methyl, or aralkyl, e.g. benzyl.

Particularly preferred anionic ligands are $H^-$, $F^-$, $Cl^-$, $Br^-$, $BF_4^-$; $PF_6^-$, $SbF_6^-$, $AsF_6^-$, $CF_3SO_3^-$, $C_6H_5$—$SO_3^-$, 4-methyl-$C_6H_4$—$SO_3^-$, 3,5-dimethyl-$C_6H_3$—$SO_3^-$, 2,4,6-trimethyl-$C_6H_2$—$SO_3^-$ and 4-$CF_3$—$C_6H_4$—$SO_3^-$ and also cyclopentadienyl ($Cp^-$). $Cl^-$ is particularly preferred.

Examples of bisanionic ligands X, X', Y and Y' are the bisanions of diols, diamines and hydroxyamines, such as catechol, N,N'-dimethyl-1,2-benzenediamine, 2-(methylamino)phenol, 3-(methylamino)-2-butanol and N,N'-bis(1,1-dimethylethyl)-1,2-ethanediamine.

In the compounds of the formulae (Ia)–(Ie) one or two neutral ligands from the group $L^1$, $L^2$, $L^{2'}$, $L^3$, $L^{3'}$, $L^5$ and $L^{5'}$ are tertiary-substituted phosphine having 3–about 40, preferably 3–30 and, with particular preference, 3–18 carbon atoms. The tertiary-substituted phosphine is preferably a compound of the formula

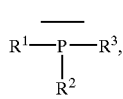 (II)

in which $R^1$, $R^2$ and $R^3$ independently of one another are $C_1$–$C_{20}$alkyl, $C_3$–$C_{12}$cycloalkyl, $C_2$–$C_{11}$heterocycloalkyl, $C_5$–$C_{12}$aryl, $C_1$–$C_{12}$heteroaryl or $C_6$–$C_{14}$aralkyl, where alkyl, cycloalkyl, heterocycloalkyl, aryl, heteroaryl and aralkyl are unsubstituted or substituted by one or more substituents of the group consisting of $C_1$–$C_6$alkyl, $C_1$–$C_6$alkoxy, $C_1$–$C_6$haloalkyl, $C_5$–$C_{12}$aryl, —$NO_2$, $SO_3^-$, ammonium and halogen; the radicals $R^1$ and $R^2$ together are unsubstituted or $C_1$–$C_6$alkyl-, $C_1$–$C_6$haloalkyl-, —$NO_2$— or $C_1$–$C_6$alkoxy-substituted tetra- or pentamethylene, which may be fused to 1 or 2 1,2-phenylene radicals, and $R^3$ is as defined above.

Examples of alkyl are methyl, ethyl and the isomers of propyl, butyl, pentyl, hexyl, heptyl, octyl, nonyl, decyl, undecyl and dodecyl. An example of aryl-substituted alkyl is benzyl. Examples of alkoxy are methoxy, ethoxy and the isomers of propoxy and butoxy.

Some examples of cycloalkyl are cyclobutyl, cycloheptyl, cyclooctyl and especially cyclopentyl and cyclohexyl. Examples of substituted cycloalkyl are methyl-, dimethyl-, trimethyl-, methoxy-, dimethoxy-, trimethoxy-, trifluoromethyl-, bis-trifluoromethyl- and tris-trifluoromethyl-substituted cyclopentyl and cyclohexyl.

Examples of aryl are phenyl and naphthyl. Examples of aryloxy are phenoxy and naphthyloxy. Examples of substituted aryl are methyl-, dimethyl-, trimethyl-, methoxy-, dimethoxy-, trimethoxy-, trifluoromethyl-, bis-trifluoromethyl- or tris-trifluoromethyl-substituted phenyl. An example of aralkyl is benzyl. Examples of substituted aralkyl are methyl-, dimethyl-, trimethyl-, methoxy-, dimethoxy-, trimethoxy-, trifluoromethyl-, bis-trifluoromethyl or tris-trifluoromethyl-substituted benzyl.

In the context of the present invention heterocycloalkyl embraces one or two and heteroaryl from one to four heteroatoms, the heteroatoms being selected from the group nitrogen, sulfur and oxygen. Some examples of heterocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl.

Preference is given to compounds of the formulae Ia–Ie in which one or two ligands from the group $L^1, L^2, L^{2'}, L^3, L^{3'}$, $L^5$ and $L^{5'}$ are tertiary-substituted phosphine of the formula II in which $R^1$, $R^2$ and $R^3$ are identical substituents, e.g. $C_1$–$C_6$alkyl or phenyl. Particular preference is given, furthermore, to radicals $R^1$, $R^2$ and $R^3$ which are sterically bulky, for example cyclic or branched, especially α,α-di-branched and very especially α-branched alkyl groups.

Another group of preferred compounds is formed by those compounds of the formulae Ia–Ie in which one or two ligands from the group $L^1$, $L^2$, $L^{2'}$, $L^3$, $L^{3'}$, $L^5$ and $L^{5'}$ independently of one another are tertiary-substituted phosphine (II) in which $R^1$, $R^2$ and $R^3$ independently of one another are $C_1$–$C_{12}$alkyl, $C_5$–$C_8$cycloalkyl, $C_6$–$C_{12}$aryl or $C_7$–$C_{13}$aralkyl in which alkyl, cycloalkyl, aryl and aralkyl are unsubstituted or substituted by one or more substituents selected from the group $C_1$–$C_6$alkyl, $C_1$–$C_6$alkoxy, $C_1$–$C_6$haloalkyl, sulfo, trimethylamino, triethylamino, ammonium and trifluoromethyl.

Within this group particular preference is given to those phosphines (II) in which $R^1$, $R^2$ and $R^3$ independently of one another are $C_1$–$C_8$alkyl, $C_5$- or $C_6$-cycloalkyl, $C_6$–$C_{10}$aryl or $C_7$–$C_{12}$aralkyl in which alkyl, cycloalkyl, aryl and aralkyl are unsubstituted or substituted by from one to three substituents selected from the group methyl, methoxy, ethyl, ethoxy and trifluoromethyl.

Particular preference is given to phosphines (II) in which $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclopentyl, cyclohexyl, phenyl, naphthyl or benzyl.

Particular preference is given to compounds (11) in which $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclopentyl, cyclohexyl, phenyl, naphthyl or benzyl, e.g. $(i\text{-}C_3H_7)_3P$, $(C_5H_9)_3P$ and $(C_6H_{11})_3P$.

In the compounds of the formulae (Ia)–(Ie) some ligands from the group $L^1$, $L^2$, $L^{2'}$, $L^3$, $L^{3'}$, $L^5$ and $L^{5'}$ are monodentate, neutral $e^-$ donor ligands having electron donor properties, two ligands from this group together are bidentate, neutral $e^-$ donor ligands and the neutral ligand from the group $L^4$ is a bidentate—or, together with two ligands of the group $L^1$, $L^2$, $L^{2'}$, $L^{3'}$, $L^5$ and $L^{5'}$, a tetradentate—neutral $e^-$ donor ligand. Such ligands are derived from unsubstituted or substituted heteroarenes from the group consisting of furan, thiophene, pyrrole, pyridine, bis-pyridine, picolylimine, γ-pyran, γ-thiopyran, phenanthroline, pyrimidine, bis-pyrimidine, pyrazine, indole, coumarone, thionaphthene, carbazole, dibenzofuran, dibenzothiophene, pyrazole, imidazole, benzimidazole, oxazole, thiazole, bis-thiazole, isoxazole, isothiazole, quinoline, bis-quinoline, isoquinoline, bis-isoquinoline, acridine, chromene, phenazine, phenoxazine, phenothiazine, triazine, thianthrene, purine, bis-imidazole and bis-oxazole.

Examples of substituents of these groups are OH, halo, —C(=O)—$OR_{s1}$, —O—C(=O)$R_{s4}$, C(=O)$R_{s2}$, nitro, $NH_2$, cyano, —$SO_3M_y$, —O—$SO_3M_y$, —N($R_{20}$)—$SO_3M_y$, —N=N—$R_{s2}$, $C_1$–$C_{12}$alkyl, $C_2$–$C_{12}$alkenyl, $C_1$–$C_{12}$alkoxy, $C_3$–$C_{12}$cycloalkyl, $C_3$–$C_{12}$cycloalkenyl, $C_2$–$C_{13}$heterocycloalkyl, $C_2$–$C_{13}$heterocycloalkenyl, $C_5$–$C_{12}$aryl, $C_5$–$C_{12}$aryloxy, $C_6$–$C_{14}$aralkyl, $C_6$–$C_{14}$aralkenyl, $C_1$–$C_9$heteroaryl, $C_2$–$C_9$heteroaryloxy, $C_2$–$C_{12}$heteroaralkyl, $C_3$–$C_{12}$heteroaralkenyl. monoamino, diamino, sulfonyl, sulfonamide, carbamide, carbamate, sulfonhydrazide, carbohydrazide, carbohydroxamic acid and aminocarbonylamide, in which $M_y$, $R_{s1}$; $R_{s2}$, $R_{s4}$ and $R_{20}$ are $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{13}$-heterocycloalkyl, $C_2$–$C_{13}$heterocycloalkenyl, $C_5$–$C_{12}$aryl, $C_5$–$C_{14}$aralkyl, $C_6$–$C_{14}$aralkenyl, $C_1$–$C_9$-heteroaryl, $C_2$–$C_{12}$heteroaralkyl or $C_3$–$C_{12}$heteroaralkenyl and $R_{s1}$, $R_{s2}$, $R_{s4}$ and $R_{20}$ are otherwise hydrogen, and alkyl, alkenyl, cycloalkyl, cycloalkenyl, heterocycloalkyl, heterocycloalkenyl, aryl, aralkyl, aralkenyl, heteroaryl, heteroalkyl or heteroaralkenyl are in turn unsubstituted or substituted by one of the specified substituents; and y is 1 and M is a monovalent metal or y is 1/2 and M is a bivalent metal cation.

In the context of the description of the present invention the terms metal and cations mean an alkali metal, for example Li, Na or K, an alkaline earth metal, for example Mg, Ca or Sr, or Mn, Fe, Zn or Ag, and the corresponding cations. Salts with lithium, sodium and potassium cations are preferred.

Monoamino, diamino, carbamide, carbamate, carbohydrazide, sulfonamide, sulfohydrazide and aminocarbonylamide correspond preferably to a group $R_8C(=O)(NH)_pN(R_9)$—, —C(=O)(NH)$_p$N$R_8R_9$, $R_8O$—C(=O)(NH)$_p$N($R_9$)—, $R_8R_{40}$N—C(=O)(NH)$_p$N($R_9$)—, —OC(=O)(NH)$_p$N$R_8R_9$, —N($R_{40}$)—C(=O)(NH)$_p$N$R_8R_9$, $R_8$S(O)$_2$(NH)$_p$N($R_9$)—; —S(O)$_2$(NH)$_p$N$R_8R_9$; $R_8R_{40}$NS(O)$_2$N($R_9$)— or —N$R_{40}$S(O)$_2$N$R_8R_9$, in which $R_8$, $R_9$ and $R_{40}$ independently of one another are hydrogen or substituents from the group OH, $C_1$–$C_{12}$alkyl, $C_2$–$C_{12}$alkenyl, $C_3$–$C_{12}$-cycloalkyl, $C_3$–$C_{12}$cycloalkenyl, $C_2$–$C_{13}$heterocycloalkyl, $C_2$–$C_{13}$heterocycloalkenyl, $C_5$–$C_{12}$aryl, $C_1$–$C_9$heteroaryl, $C_6$–$C_{14}$aralkyl, $C_7$–$C_{14}$aralkenyl with $C_2$–$C_6$alkenylene and $C_5$–$C_{12}$aryl, $C_6$–$C_{15}$-heteroaralkyl, $C_5$–$C_{14}$heteroaralkenyl and di-$C_6$–$C_{10}$aryl-$C_1$–$C_6$alkyl, and in which in the group $R_8R_9$N the substituents $R_{8'}$ and $R_{9'}$ independently of one another are hydrogen or substituents from the group OH, $SO_3M_y$, $OSO_3M_y$, $C_1$–$C_{12}$alkyl, $C_3$–$C_{12}$cycloalkyl, $C_2$–$C_{11}$heterocycloalkyl, $C_6$–$C_{10}$aryl, $C_5$–$C_9$heteroaryl, $C_7$–$C_{11}$aralkyl, $C_6$–$C_{10}$heteroaralkyl, $C_8$–$C_{16}$aralkenyl with $C_2$–$C_6$-alkenylene and $C_6$–$C_{10}$aryl and di-$C_6$–$C_{10}$aryl-$C_1$–$C_6$alkyl, which are unsubstituted or substituted by one or more substituents from the group OH, halo, —C(=O)—$OR_{s1}$, —O—C(=O)$R_{s4}$, —C(=O)$R_{s2}$, nitro, $NH_2$, cyano, —$SO_3M_y$, —O—$SO_3M_y$, —N($R_{20}$)—$SO_3M_y$, —N=N—

$R_{s2}$, $C_1$–$C_{12}$alkyl, $C_2$–$C_{12}$alkenyl, $C_1$–$C_{12}$alkoxy, $C_3$–$C_{12}$cycloalkyl, $C_3$–$C_{12}$cycloalkenyl, $C_2$–$C_{13}$heterocycloalkyl, $C_2$–$C_{13}$-heterocycloalkenyl, $C_5$–$C_{12}$aryl, $C_5$–$C_{12}$aryloxy, $C_6$–$C_{14}$aralkyl, $C_6$–$C_{14}$aralkoxy, $C_7$–$C_{14}$aralkenyl, $C_1$–$C_9$heteroaryl, $C_2$–$C_9$heteroaryloxy, $C_2$–$C_{12}$heteroaralkyl, $C_3$–$C_{12}$heteroaralkenyl, monoamino, diamino, sulfonyl, sulfonamide, carbamide, carbamate, sulfohydrazide, carbohydrazide, the carbohydramic acid radical and aminocarbonylamide radical, in which $M_y$, $R_{s1}$, $R_{s2}$, $R_{s4}$ and $R_{20}$ are $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{13}$-heterocycloalkyl, $C_2$–$C_{11}$heterocycloalkenyl, $C_6$–$C_{12}$aryl, $C_6$–$C_{13}$aralkyl, $C_6$–$C_{13}$aralkenyl, $C_1$–$C_9$-heteroaryl, $C_2$–$C_{12}$heteroaralkyl or $C_3$–$C_{12}$heteroaralkenyl and $R_{s1}$, $R_{s2}$, $R_{s4}$ and $R_{20}$ are otherwise hydrogen, and alkyl, alkenyl, cycloalkyl, cycloalkenyl, heterocycloalkyl, heterocycloalkenyl, aryl, aralkyl, aralkenyl, heteroaryl, heteroaralkyl or heteroaralkenyl in turn are unsubstituted or substituted by one of the specified substituents; and y is 1 and M is a monovalent metal or y is 1/2 and M is a divalent metal; or $R_8$ and $R_9$ or $R_{8'}$ and $R_{9'}$ or $R_8$ and $R_{40}$ in the case of —$NR_8R_9$ or —$NR_{8'}R_{9'}$ or $R_8R_{40}N$— together are tetramethylene, pentamethylene, —$(CH_2)_2$—O—$(CH_2)_2$—, —$(CH_2)_2$—S—$(CH_2)_2$— or —$(CH_2)_2$—$NR_7$—$(CH_2)_2$—, and $R_7$ is hydrogen, $C_1$-$C_6$alkyl, $C_6$–$C_{13}$aralkyl, —C(=O)$R_{s2}$ or sulfonyl.

The sulfonyl substituent corresponds, for example, to the formula $R_{10}$—$SO_2$— in which $R_{10}$ is $C_1$–$C_{12}$alkyl, $C_3$–$C_{12}$cycloalkyl, $C_2$–$C_{11}$heterocycloalkyl, $C_5$–$C_{12}$aryl, $C_1$–$C_9$heteroaryl, $C_6$–$C_{13}$-aralkyl or $C_2$–$C_{13}$heteroaralkyl which is unsubstituted or substituted by one or more substituents from the group OH, halo, —C(=O)—$OR_{s1}$, —O—C(=O)$R_{s4}$, —C(=O)$R_{s2}$, nitro, $NH_2$, cyano, —$SO_3M_y$, —O—$SO_3M_y$, —$N(R_{20})$—$SO_3M_y$, —N=N—$R_{s2}$, $C_1$–$C_{12}$alkyl, $C_2$–$C_{12}$alkenyl, $C_1$–$C_{12}$-alkoxy, $C_3$–$C_{12}$cycloalkyl, $C_3$–$C_{12}$cycloalkenyl, $C_2$—$C_{13}$heterocycloalkyl, $C_2$—$C_{13}$-heterocycloalkenyl, $C_5$–$C_{12}$aryl, $C_5$–$C_{12}$aryloxy, $C_6$–$C_{13}$aralkyl, $C_6$–$C_{13}$aralkoxy, $C_6$–$C_{13}$-aralkenyl, $C_1$–$C_9$heteroaryl, $C_2$–$C_9$heteroaryloxy, $C_2$–$C_{12}$heteroaralkyl, $C_3$–$C_{12}$heteroaralkenyl, monoamino, diamino, sulfonyl, sulfonamide, carbamide, carbamate, sulfohydrazide, carbohydrazide, the carbohydroxamic acid radical and aminocarbonylamide radical, in which $M_y$, $R_{s1}$, $R_{s2}$, $R_{s4}$ and $R_{20}$ are $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{13}$-heterocycloalkyl, $C_2$–$C_{13}$heterocycloalkenyl, $C_5$–$C_{12}$aryl, $C_6$–$C_{13}$aralkyl, $C_6$–$C_{13}$aralkenyl, $C_1$–$C_9$-heteroaryl, $C_2$–$C_{12}$heteroaralkyl or $C_3$–$C_{12}$heteroaralkenyl and $R_{s1}$, $R_{s2}$, $R_{s4}$ and $R_{20}$ are otherwise hydrogen, and alkyl, alkenyl, cycloalkyl, cycloalkenyl, heterocycloalkyl, heterocycloalkenyl, aryl, aralkyl, aralkenyl, heteroaryl, heteroaralkyl or heteroaralkenyl in turn are unsubstituted or substituted by one of the specified substituents; and y is 1 and M is a monovalent metal or y is 1/2 and M is a divalent metal cation.

Preferred monodentate and bidentate $e^-$ donor ligands are derived, for example, from heteroarenes of the group:

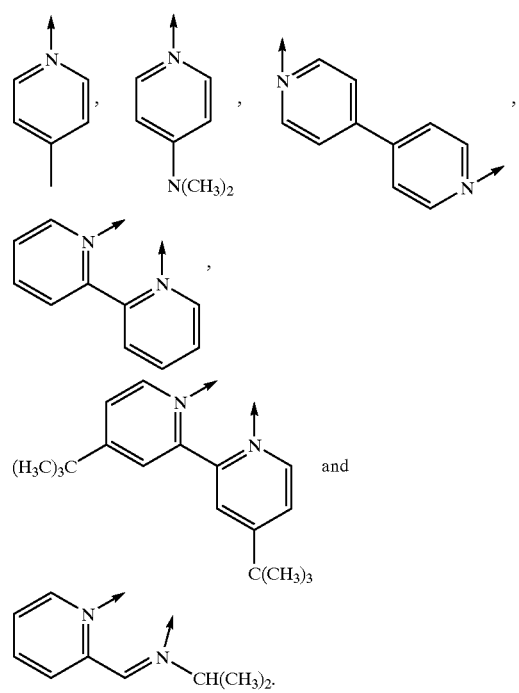

A preferred group is formed by those compounds of the formulae Ia–Ie in which one or two ligands from the group $L^1, L^2, L^{2'}, L^3, L^{3'}, L^5$ and $L^{5'}$ in each case independently of one another are monodentate pyridine which is unsubstituted or substituted by one or more substituents from the group $C_1$–$C_{12}$alkyl $C_2$–$C_{11}$heterocycloalkyl, $C_5$–$C_9$heteroaryl, monoamino, diamino and —C(=O)H. Examples of such ligands are

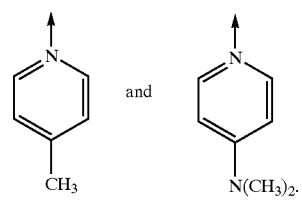

Another preferred group of compounds is formed by compounds of the formulae Ia–Ie, in which two of the ligands $L^1, L^2, L^{2'}, L^3, L^{3'}, L^5$ and $L^{5'}$ together are bidentate bis-pyridine, phenanthrolinyl, bis-thiazolyl, bis-pyrimidine or picolylimine, which are unsubstituted or substituted by one or more substituents from the group $C_1$–$C_{12}$alkyl, $C_6$–$C_{10}$aryl and cyano where the substituents alkyl and aryl in turn are unsubstituted or substituted by one or more substituents from the group $C_1$–$C_{12}$alkyl, nitro, monoamino, diamino and nitro- or secondary amino-substituted —N=N—$C_6$–$C_{10}$aryl. Examples of such ligands are

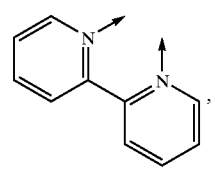

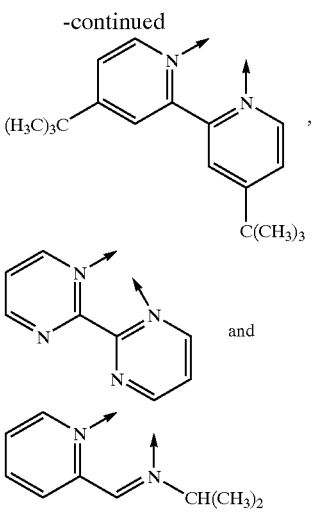

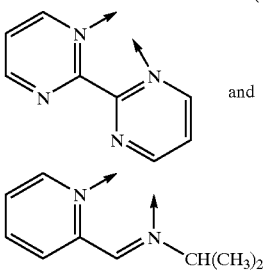

and

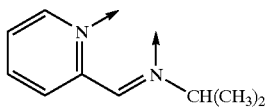

Another preferred group of compounds is formed by compounds of the formulae Ia–Ie, in which $L^4$ is bidentate bipyridine or together with two of the ligands $L^1, L^2, L^{2'}, L^3$, $L^5$ and $L^{5'}$ is tetradentate bipyrimidine, which are unsubstituted or substituted by one or more substituents from the group $C_1$–$C_{12}$alkyl, $C_2$–$C_{11}$heterocycloalkyl, $C_5$–$C_9$heteroaryl, monoamino, diamino and —C(=O)H. One example of a tetradentate ligand of this type is

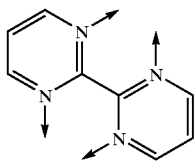

A further preferred group of compounds is formed by compounds of the formulae Ia–Ie, in which two of the ligands $L^1$, $L^2$, $L^{2'}$, $L^3$, $L^{3'}$, $L^5$ and $L^{5'}$ together, or $L^4$, is bidentate pyridine which is unsubstituted or substituted by one or more substituents from the group $C_1$–$C_{12}$alkyl, $C_2$–$C_{11}$heterocycloalkyl, $C_5$–$C_9$heteroaryl, monoamino, diamino and —C(=O)H. One example of a ligand of this type is

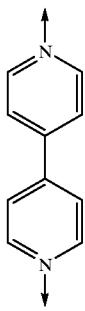

In compounds of the formula Ia Z is sulfur or the groups

and

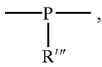

in which R''' is hydrogen or a hydrocarbon radical. The term hydrocarbon radical for R''' embraces the definitions given earlier for $R^1$, $R^2$ and $R^3$ under compounds (II), especially the aliphatic, cycloaliphatic or cycloaliphatic-aliphatic radicals, carbocyclic aryl radicals or aryl-aliphatic radicals specified there with the further substituents which were likewise mentioned, and also the heterocyclic groups defined under the ligands of the group $L^1, L^2, L^{2'}, L^3, L^{3'}, L^5$ and $L^{5'}$ with the further substituents specified there. Provided that Z has the definitions of A or A', R is a hydrocarbon radical having the definitions specified for R'''.

If Z in compounds of the formula Ia is sulfur, R is aryl, for example unsubstituted phenyl or phenyl which is substituted by one or more substituents from the group consisting of $C_1$–$C_6$-alkyl, $C_1$–$C_6$alkoxy, carboxyl, $C_1$–$C_6$alkoxycarbonyl, $C_1$–$C_6$haloalkyl, nitro, sulfo, ammonium and halo.

In compounds of the formulae Ia Z can also be the groups A and A', in which R''' is preferably hydrogen, $C_1$–$C_{20}$alkyl, $C_3$–$C_8$cycloalkyl, $C_3$–$C_7$heterocycloalkyl, $C_5$–$C_{12}$aryl or $C_1$–$C_9$heteroaryl, in which alkyl, cycloalkyl, heterocycloalkyl, aryl and heteroaryl are unsubstituted or substituted by one or more substituents from the group $C_1$–$C_6$alkyl, $C_1$–$C_6$haloalkyl, $C_1$–$C_6$alkoxy, carboxyl, $C_1$–$C_6$alkoxycarbonyl, $C_5$–$C_{12}$aryl, $C_5$–$C_{12}$aryloxy, —NO$_2$ and halo. R in this case is a hydrocarbon radical having the definitions specified for R'''.

In compounds of the formulae Ib–Ie $Z^1$ and $Z^{1'}$ independently of one another are oxygen, sulfur or the groups A and A' having the specified definitions.

If $Z^1$ and $Z^{1'}$ in compounds of the formulae Ib–Ie have these definitions, R' and R'' are hydrocarbon radicals having the definitions specified for R under A and A', especially the aliphatic, cycloaliphatic or cycloatiphatic-aliphatic radicals, carbocyclic aryl radicals or arylaliphatic radicals specified there with the further substituents specified there. In dimeric compounds of the formulae Ic, Id and Ie, R and R can also be bridged with one another by way, for example, of $C_2$–$C_{10}$alkylene groups which can in turn be substituted by functional groups, e.g. halo, hydroxyl, alkoxy, etc.

In compounds of the formulae Ib–Ie R' and R'' are preferably $C_1$–$C_{20}$alkyl, $C_3$–$C_8$cycloalkyl, $C_3$–$C_7$heterocycloalkyl, $C_5$–$C_{12}$aryl or $C_1$–$C_9$heteroaryl, in which alkyl, cycloalkyl, heterocycloalkyl, aryl and heteroaryl are unsubstituted or substituted by one or more substituents from the group $C_1$–$C_6$alkyl, $C_1$–$C_6$haloalkyl, $C_1$–$C_6$alkoxy, carboxyl, $C_1$–$C_6$alkoxycarbonyl, $C_5$–$C_{12}$aryl, $C_5$–$C_{12}$aryloxy, —NO$_2$ and halo. If $Z^1$ and $Z^{1'}$ in compounds of the formulae Ib–Ie are the groups A and A', R''' therein has the preferred definitions specified for R' and R''.

Furthermore, if Z, $Z^1$ or $Z^{1'}$ in compounds of the formulae Ia–Ie has the definition of the groups A and A', the substituents R''' and R or R' and R'', including phosphorus or preferably nitrogen of the group Z, can be joined to one another to form a heterocycle which can be unsaturated, partly saturated or fully saturated and can carry further substituents, e.g. alkyl, alkoxy, halo, hydroxyl or oxo. This case is illustrated by the following example:

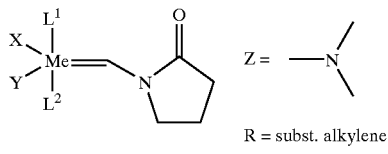

R = subst. alkylene

The invention preferably provides compounds of the formulae

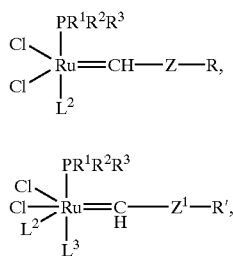
(I'a)

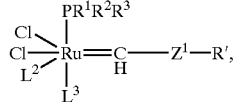
(I'b)

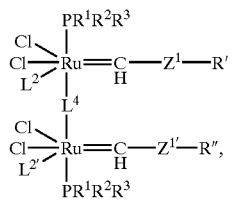
(I'c)

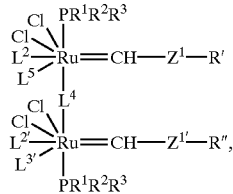
(I'd)

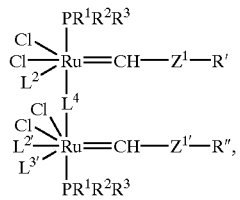
(I'e)

according to claim 1
in which $L^2$, $L^{2'}$, $L^3$, $L^{3'}$ and $L^5$ independently of one another are monodentate, neutral e⁻ donor ligands; $L^4$ is a bidentate—or, together with two of the ligands $L^2$, $L^{2'}$, $L^{3'}$ and $L^5$, a tetradentate—neutral e⁻ donor ligand; $R^1$, $R^2$ and $P^3$ independently of one another are $C_1$–$C_{20}$alkyl, $C_3$–$C_{12}$cycloalkyl, $C_2$–$C_{11}$heterocycloalkyl, $C_5$–$C_{12}$aryl, $C_1$–$C_9$heteroaryl or $C_6$–$C_{13}$aralkyl, and alkyl, cycloalkyl, heterocycloalkyl, aryl, heteroaryl and aralkyl are unsubstituted or substituted by one or more substituents from the group consisting of $C_1$–$C_6$alkyl, $C_1$–$C_6$alkoxy, carboxyl, $C_1$–$C_6$alkoxycarbonyl, $C_1$–$C_6$haloalkyl, $C_5$–$C_{12}$aryl, $C_5$–$C_{12}$-aryloxy, —$NO_2$, sulfo, ammonium and halo; the radicals $R^1$ and $R^2$ together are unsubstituted or $C_1$–$C_6$alkyl-, $C_1$–$C_6$haloalkyl-, —$NO_2$— or $C_1$–$C_6$alkoxy-substituted tetra- or pentamethylene, or are unsubstituted or $C_1$–$C_6$alkyl-, $C_1$–$C_6$haloakyl-, —$NO_2$ or $C_1$–$C_6$alkoxy-substituted tetra- or pentamethylene which are fused to one or two 1,2-phenylenes, and $R^3$ is as defined;

Z is sulfur or the group

(A')

in which R'" is hydrogen or a hydrocarbon radical from the group $C_1$–$C_{20}$alkyl, $C_3$–$C_8$-cycloalkyl, $C_3$–$C_8$heterocycloalkyl, $C_5$–$C_{12}$aryl, $C_1$–$C_9$heteroaryl and $C_6$–$C_{13}$aralkyl, in which alkyl, cycloalkyl, heterocycloalkyl, aryl and heteroaryl are unsubstituted or substituted by $C_1$–$C_6$alkyl, $C_1$–$C_6$haloalkyl, $C_1$–$C_6$alkoxy, carboxyl, $C_1$–$C_6$alkoxycarbonyl, $C_5$–$C_{12}$aryl, $C_5$–$C_{12}$-aryloxy, —$NO_2$ or halo;

$Z^1$ and $Z^{1'}$ independently of one another are oxygen, sulfur or the groups

(A)

and A' with the definitions specified for R'";

R is substituted or substituted aryl if is sulfur or is a hydrocarbon radical having the definitions specified for R'" if Z has the definition of the groups A and A'; and R' and R'" are a hydrocarbon radical having the definitions specified for R'", or an isomer of this compound;

with the exception of compounds (I'b), wherein one of $L^2$ and $L^3$ represents carbonyl.

The invention preferably provides a selected group of compounds of the formulae I'a–I'e, in which $L^2$, $L^{2'}$, $L^3$ and $L^{3'}$ independently of one another are pyridyl which is unsubstituted or substituted by one or more substituents from the group $C_1$–$C_{12}$alkyl, $C_3$–$C_{11}$heterocycloalkyl, $C_1$–$C_9$heteroaryl, monoamino, diamino and —C(=O)H; or two ligands $L^2$, $L^{2'}$, $L^3$ and $L^{3'}$ together are bis-pyridine, phenanthroline, bis-thiazole, bis-pyrimidine, bis-quinoline or picolylimine which are unsubstituted or substituted by one or more substituents from the group $C_1$–$C_{12}$alkyl, $C_6$–$C_{10}$aryl and cyano, where the substituents alkyl and aryl are in turn unsubstituted or substituted by one or more substituents from the group $C_1$–$C_{12}$alkyl, nitro, monoamino, diamino and nitro- or diamino-substituted —N=N— $C_6$–$C_{10}$aryl; $L^4$ is bis-pyridine or bis-pyrimidine:

$R^1$, $R^2$ and $R^3$ are isopropyl, sec-butyl, cyclopentyl or cyclohexyl;

Z is sulfur or groups A and A', in which R'" is hydrogen, $C_1$–$C_4$alkyl, phenyl or $C_1$–$C_4$-alkyl-substituted phenyl;

$Z^1$ and $Z^{1'}$ independently of one another are oxygen, sulfur or the groups A and A' with the definitions specified for R'";

R is phenyl if Z is sulfur or is $C_1$–$C_4$alkyl, phenyl or $C_1$–$C_4$alkyl-substituted phenyl if Z has the definition of the groups A and A'; and R' and R" are $C_1$–$C_4$alkyl, phenyl or $C_1$–$C_4$alkyl-substituted phenyl, and isomers of these compounds.

The invention likewise preferably provides the specified compounds of the formulae Ia–Ie, in which Z and/or $Z^1$ or $Z^{1'}$ has the definition of the groups A and A', the substituents R'" and R and/or R' and R" including nitrogen from the group Z and/or $Z^1$ or $Z^{1'}$ are joined to one another to form a heterocycle which is unsaturated, partly saturated or fully saturated and can carry further substituents, for example alkyl, alkoxy, halo, hydroxyl or oxo.

The invention likewise preferably provides the compounds specified in the Examples, e.g. dichlorobis[tricyclohexylphosphino]phenylthiomethinoruthenium or dichlorobis[tricyclohexylphosphino]-1-(2-oxopyrrolidino)methinoruthenium and isomers of these compounds.

The invention likewise provides a process for preparing compounds of the formulae Ia–Ie according to claim 1, which comprises replacing the ligand $L^2$ or $L^3$ in a compound of the formula

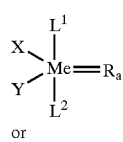

(IIIa)

or

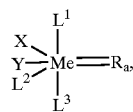

(IIIb)

in which $R_a$ is an eliminable leaving group of the substrate and X, Y, $L^1$, $L^2$ and $L^3$ are as defined for the formulae Ia and Ib with a vinyl ether, vinyl thioether, vinylamine or vinylphosphine of the formula

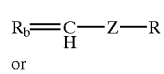

(IVa)

or

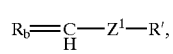

(IVb)

in which $R_b$ is an eliminable leaving group of the reagent and Z, $Z^1$, R and R' are as defined for formulae Ia and Ib, and, if desired, for the preparation of dimeric compounds of the formulae Ic, Id and Ie, replacing the ligand $L^2$ or $L^3$ by a bidentate or tetradentate ligand $L^4$, and/or substituting the groups X, X', Y and Y' and also $L^1$, $L^2$, $L^{2'}$, $L^3$, $L^{3'}$, $L^5$ and $L^{5'}$ in an obtainable compound of the formulae Ia–Ie.

The process of the invention is advantageously conducted in such a way that the compounds of the formulae IIIa and IIIb are dissolved in a solvent and then the desired vinyl ether, vinyl thioether, vinylamine or vinylphosphine (IVa) or (IVb) is added. The mass ratio of compounds (IIIa) and (IIIb) to compounds (IVa) and (IVb) is generally within the range from 1:1 to 1:100, preference being given to a ratio in the range from 1:1 to 1:5. The reaction takes place within a temperature range from −80° C. to 150° C., preferably from 0° C. to 100° C. and, with particular preference, at from room temperature to 50° C.

The invention likewise provides a composition comprising (α) dicyclopentadiene or another strained cycloolefin, or dicyclopentadiene in a mixture with another strained cycloolefin, and (β) a catalytic amount of at least one compound of the formulae Ia–Ie, in which Me and Me' independently of one another are ruthenium or osmium and X, X', Y, Y', $L^1$, $L^2$, $L^{2'}$, $L^3$, $L^{3'}$, $L^4$, $L^5$ and $L^{5'}$, Z, $Z^1$ $Z^{1'}$, R, R' and R" are as defined, and isomers of these compounds and, if desired, further additives for polymers.

Dicyclopentadiene is the dimer of cyclopentadiene, which is known and commercially available and has the formula

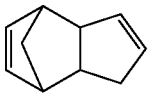

it is known that, together with further cyclopentadiene, dicyclopentadiene forms so-called Diels-Alder adducts and hence forms oligomers which can likewise be used. In accordance with the invention the composition may comprise pure dicyclopentadiene, oligomers of dicyclopentadiene or mixtures thereof. The oligomers are of the formula

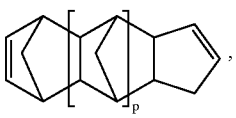

in which p is from 1 to 100, preferably from 1 to 50, with particular preference from 1 to 20 and, with especial preference, from 1 to 10.

The cycloolefins known as strained cycloolefins, which may be present as comonomers in the composition of the invention, are known.

The cyclic olefins can be monocyclic or polycyclic, fused and/or bridged ring systems, which have, for example, from two to four rings and which are unsubstituted or substituted and can contain heteroatoms such as O, S, N or Si, for example, in one or more rings and/or can contain fused aromatic or heteroaromatic rings, such as o-phenylene, o-naphthylene, o-pyridinylene or o-pyrimidinylene. The individual cyclic rings include 3 to 16, preferably 3 to 12 and, with particular preference, 3 to 8 ring members. The cyclic olefins may contain further nonaromatic double bonds, preferably from 2 to 4 such additional double bonds depending on ring size. The ring substituents involved are those which are inert; in other words, those which do not impair the chemical stability of the ruthenium and osmium compounds. The cycloolefins are strained rings or ring systems.

If the cyclic olefins contain more than one double bond, for example 2 to 4 double bonds, then depending on the reaction conditions, on the chosen monomer and on the amount of catalyst it is also possible for crosslinked polymers to form.

Fused-on alicyclic rings contain preferably 3 to 8, more preferably 4 to 7 and, with particular preference, 5 or 6 ring carbon atoms.

The cyclic olefins which are present in the composition and which may be polymerized with the aid of the catalysts of the invention are known and are described, for example, in WO 96/20235.

The comonomeric cycloolefins can be present in an amount of from 0.01 to 99% by weight, preferably from 0.1 to 95% by weight, with particular preference from 1 to 90% by weight and, with especial preference, from 5 to 80% by weight, based on the monomers present in the composition. Very particular preference is given to norbornene as comonomer in amounts, for example, of from 20 to 60% by weight.

The dienes which are present in the composition and which can be ring-closed with the aid of the catalysts of the invention are described, for example, in Miller et al. [Miller, S. J., Blackwell, H. E., Grubbs, R. H., *J. Am. Chem. Soc.* 118:9606–9614 (1996)] or in Grubbs et al. [Grubbs, R. H., Miller, S. J., Fu, G. C., *Acc. Chem. Res.* 28:446–452 (1995)].

The catalysts of the invention can also be used for breaking down unsaturated polymers or for isomerizing double bonds, as has already been described for ruthenium catalysts in McGrath and Grubbs [McGrath, D. V., Grubbs, R. H., *Organometallics* 13:224 (1994)].

The composition of the invention can comprise inert solvents. One particular advantage is that in the case of liquid monomers metathesis polymerization can be carried out without the use of a solvent. A further advantage is that the polymerization can even be carried out in water, polar and protic solvents or water/solvent mixtures. In such cases it is of advantage, in the context of the present invention, to use a surfactant.

Examples of suitable inert solvents are protic polar and aprotic solvents, which can be used alone or in mixtures of at least two solvents. Examples are ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons, etc.

Compositions of the invention comprising a DCPD are insensitive to oxygen and moisture, which permits storage and reaction without an inert gas.

In the context of the present invention, catalytic amounts denote preferably an amount from 0.001 to 20 mol-%, with particular preference from 0.01 to 15 mol-% and, with very particular preference, from 0.01 to 10 mol-%, based on the amount of monomer. On the basis of the high thermocatalytic activity, very particular preference is given to amounts from 0.001 to 2 mol-%.

The composition of the invention which is used for the polymerization can be prepared directly prior to polymerization or can be used as a preformulated mixture, since the catalysts used are of particularly high stability. The mixture may even be stored for a prolonged period prior to polymerization, as a ready-to-use formulation, which is of advantage for large-scale industrial use.

The composition of the invention can comprise additives suitable for polymers, which additives are preferably used as formulating auxiliaries to improve the chemical and physical properties. The auxiliaries can be present in surprisingly high proportions without adversely affecting the polymerization; for example, in amounts of up to 70% by weight, preferably from 1 to 70% by weight, more preferably from 5 to 60% by weight, with particular preference from 10 to 50% by weight and with especial preference from 10 to 40% by weight, based on the composition. Such auxiliaries have been disclosed in large numbers and are set out by way of example in the following list of auxiliaries:

1. Antioxidants
1.1. Alkylated Monophenols,
for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or sidechain-branched nonylphenols; such as 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols,
for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.
1.3. Hydroquinones and Alkylated Hydroquinones,
for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.
1.4. Tocopherols,
for example α-tocopherol, β-tocopherol, γ-tocopherol, δ-tocopherol and mixtures thereof (vitamin E).
1.5. Hydroxylated Thiodiphenyl Ethers,
for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.
1.6. Alkylidenebisphenols,
for example 2,2'-methylenebis(6-tert-butyl-4-methylphenol), 2,2'-methylenebis(6-tert-butylethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzy)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.
1.7. O-, N- and S-benzyl Compounds,
for example 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl 3,5-di-tert-butyl-4-hydroxybenzylmercaptoacetate.
1.8. Hydroxybenzylated Malonates,
for example dioctadecyl 2,2-bis(3,5-di-tert-butyl-2-hydroxybenzyl)malonate, dioctadecyl 2-(3-tert-butyl-4-hydroxy-5-methylbenzyl)malonate, didodecyl mercaptoethyl-2,2-bis(3,5-di-tert-butyl-4-hydroxybenzyl)malonate, di-[4-(1,1,3,3-tetramethylbutyl)phenyl] 2,2-bis(3,5-di-tert-butyl-4-hydroxybenzyl)malonate.
1.9. Aromatic Hydroxybenzyl Compounds,
for example 1,3,5-tris(3,5-di-tert-butyl-4-hydroxybenzyl)-2,4,6-trimethylbenzene, 1,4-bis(3,5- di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-Di-tert-butyl-4-hydroxyphenyl) propionic Acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-Tert-butyl-4-hydroxy-3-methylphenyl) propionic Acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-Dicyclohexyl-4-hydroxyphenyl) propionic Acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-Di-tert-butyl-4-hydroxyphenylacetic Acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-Di-tert-butyl-4-hydroxyphenyl) propionic Acid, e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard® XL-1 from Uniroyal).

1.18. Ascorbic Acid (vitamin C).

1.19. Aminic Antioxidants, for example N,N'-diisopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diamino-diphenylmethane, 1,2-di[(2-methylphenyl)amino]ethane, 1,2-di(phenylamino)propane, (o-tolyl)biguanide, di-[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono and dialkylated dodecyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octyl-phenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl) sebacate, 2,2,6, 6-tetramethylpiperidin-4-one and 2,2,6,6-tetramethylpiperidin-4-ol.

2. UV Absorbers and Light Stabilizers 2.1. 2-(2'-Hydroxyphenyl)benzotriazoles, for example 2-(2'-hydroxy-5'-methylphenyl) benzotriazole, 2-(3',5'-di-tert-butyl-2'-hydroxyphehyl) benzotriazole, 2-(5'-tert-butyl-2'-hydroxyphenyl) benzotnazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl] benzotriazole with polyethylene glycol 300;

[R—CH$_2$CH$_2$—COO—CH$_2$CH$_2$-]$_2$ where R=3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl) phenyl]benzotriazole.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of Substituted or Unsubstituted Benzoic Acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxy-cinnamate or butyl α-cyano-β-methyl-p-methoxycinnamate, methyl α-carbomethoxy-p-methoxycinnamate and N-β-carbomethoxy-β-cyanovinyl)-2-methylindoline.

2.5. Nickel Compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically Hindered Amines, for example bis(2,2,6,6-tetramethylpiperidin-4-yl) sebacate, bis(2,2,6,6-tetramethylpiperidin-4-yl) succinate, bis(1,2,2,6,6-pentamethylpiperidin-4-yl) sebacate, bis(1-octyloxy-2,2,6,6-tetramethylpiperidin-4-yl)sebacate, bis(1,2,2,6,6-pentamethylpiperidyl)n-butyl-3,5-di-tert-butyl-4-hydroxybenzylmalonate, the condensate of 1-hydroxyethyl-2,2,6,6-tetramethyl-4-hydroxypiperidine and succinic acid, the linear or cyclic, condensates of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis (1-octyloxy-2,2,6,6-tetramethylpiperidyl)sebacate, bis (1-octyloxy-2,2,6,6-tetramethylpiperidyl)succinate, the linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)-hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4.5]decane, the reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl)ether, N,N'-bisformyl-N,N'-bis(2,2,6,6-tetramethyl-4-piperidyl)-hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, the reaction product of maleic anhydride-α-olefin copolymer and 2,2,6,6-tetramethyl-4-aminopiperidine or 1,2,2,6,6-pentamethyl-4-aminopiperidine.

2.7. Oxalamides, for example 4,4'-dioctyloxyoxanilide, 2,2'-diethoxy-oxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy- and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal Deactivators for example, N,N'-diphenyloxalamide, N-salicylal-N'-salicyloyl hydrazine, N,N'-bis(salicyloyl)hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites, Phosphines and Phosphonites for example triphenyl phosphite, diphenyl alkyl phosphites, phenyl dialkyl phosphites, tris(nonylphenyl)phosphite, trilauryl phosphite, trioctadecyl phosphite, trimethylphosphine, tri-n-butylphosphine, triphenylphosphine, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl) pentaerythritol diphosphite, bisisodecyloxypentaerythritol diphosphite, bis(2,4-di-tert-butyl-6-methylphenyl) pentaerythritol diphosphite, bis(2,4,6-tri-tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyldibenzo[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo[triethyl-tris(3,3',5,5"tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite.

Particular preference is given to using the following phosphites:

Tris(2,4-di-tert-butylphenyl)phosphite(Irgafos®168, Ciba-Geigy), tris(nonylphenyl)phosphite,

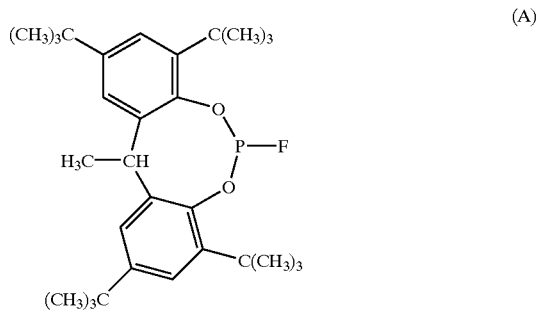

(A)

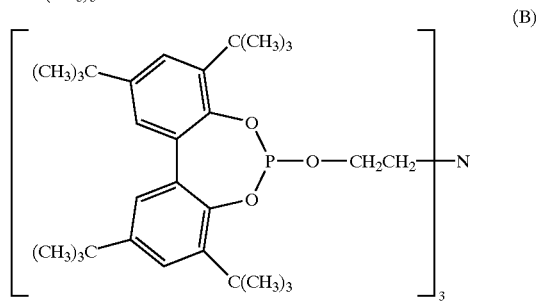

(B)

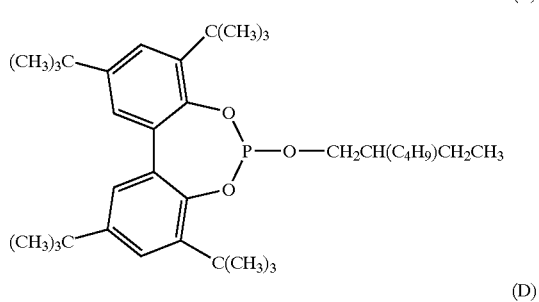

(C)

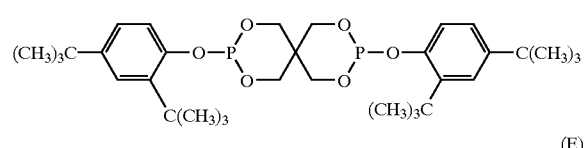

(D)

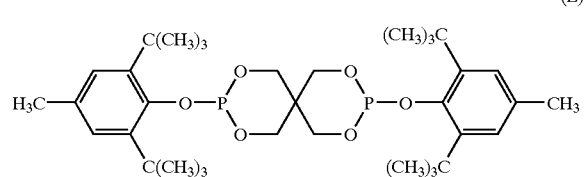

(E)

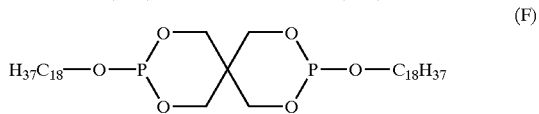

(F)

-continued

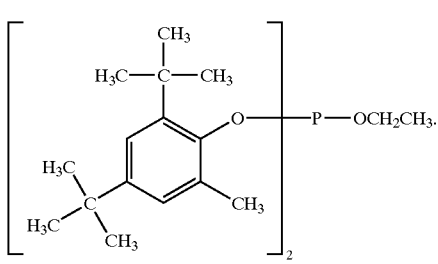

(G)

5. Hydroxylamines for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones for example N-benzyl alpha-phenyl nitrone, N-ethyl alpha-methyl nitrone, N-octyl alpha-heptyl nitrone, N-lauryl alpha-undecyl nitrone, N-tetradecyl alpha-tridecyl nitrone, N-hexadecyl alpha-pentadecyl nitrone, N-octadecyl alpha-heptadecyl nitrone, N-hexadecyl alpha-heptadecyl nitrone, N-octadecyl alpha-pentadecyl nitrone, N-heptadecyl alpha-heptadecyl nitrone, N-octadecyl alpha-hexadecyl-nitrone, and nitrones derived from N,N-dialkylhydroxylamines prepared from hydrogenated tallow fatty amines.

7. Thiosynergists for example dilauryl thiodiproprionate or distearyl thiodipropionate.

8. Peroxide Scavengers for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis(β-dodecylmercapto)propionate.

9. Polyamide Stabilizers for example copper salts in combination with iodides and/or phosphorus compounds and salts of divalent manganese.

10. Basic Co-stabilizers for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating Agents for example inorganic substances, such as talc, metal oxides such as titanium dioxide or magnesium oxide, phosphates, carbonates or sulfates of, preferably, alkaline earth metals; organic compounds such as mono- or polycarboxylic acids and their salts, such as 4-tert-butylbenzoic acid, adipic acid, diphenyl acetic acid, sodium succinate or sodium benzoate; and polymeric compounds, for example ionic copolymers (ionomers).

12. Fillers and Reinforcing Agents for example calcium carbonate, silicates, glass fibres, glass beads, talc, kaolin, mica, barium sulfate, metal oxides and hydroxides, carbon black, graphite, wood flour and flours or fibres of other natural products, and synthetic fibres.

13. Other Additives for example plasticizers, lubricants, emulsifiers, pigments, rheological additives, catalysts, levelling assistants, optical brighteners, flameproofing agents, antistatic agents, blowing agents.

14. Benzofuranones and Indolinones as described, for example, in U.S. Pat. No. 4,325,863; U.S. Pat. No. 4,338,244; U.S. Pat. No. 5,175,312, U.S. Pat. No. 5,216,052; U.S. Pat. No. 5,252,643; DE-A-4316611; DE-A-4316622; DE-A-4316876; EP-A-0589839 or EP-A-0591102, or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The invention provides, furthermore, a process for preparing metathesis polymers, which comprises heating a composition comprising (α') dicyclopentadiene or another strained cycloolefin, or dicyclopentadiene in a mixture with another strained cycloolefin, and (β') a catalytic amount of at least one compound of the formulae Ia–Ie, in which Me and Me independently of one another are ruthenium or osmium and X, X', Y, Y', $L^1, L^2, L^{2'}, L^3, L^{3'}, L^4, L^5$ and $L^{5'}, Z, Z^1 Z^{1'}, R, R'$ and R" are as defined, and isomers of these compounds and, if desired, further additives for polymers and, if desired, subjecting the obtainable metathesis polymer to a shaping process.

The process of the invention is preferably carried out at a temperature of at least 0° C. In particular, the process of the invention is conducted at temperatures from 0° to 300° C., preferably at from room temperature to 250° C., with particular preference from room temperature to 200° C. and, with especial preference, at from room temperature to 160° C. Following polymerization it may be advantageous to condition the polymers at elevated temperatures, for example from 80 to 200° C. To prepare linear polymers the reaction is preferably carried out in dilute solutions.

Polymerization can be associated with shaping processes such as calendering, casting, compression moulding, injection moulding or extrusion, for example. With the process of the invention it is possible to produce materials for the machining production of shaped articles or thermoplastically deformable materials for producing mouldings of all kinds and coatings. Advantageously, shaping and polymerization are connected in solvent-free reactive systems, it being possible to employ processing techniques such as injection moulding, extrusion, polymerization in predetermined forms (possibly under superatmospheric pressure), for example.

The invention also provides the polymers obtainable by the process of the invention.

Of the polymers, preference is given to those containing only carbon and hydrogen.

The polymers prepared by the process of the invention can be homopolymers or copolymers with random distribution of the structural units, graft polymers or block polymers, and crosslinked polymers of this kind. They may have an average molecular weight ($\overline{Mw}$) of, for example, from 500 to 2 million daltons, preferably from 1000 to 1 million daltons (determined by GPC by comparison with polystyrene standards of narrow distribution).

It has surprisingly been found that the polymerization leads in high yields to a polydicyclopentadiene which corresponds to a linear polymer or copolymer having structural units of the formula

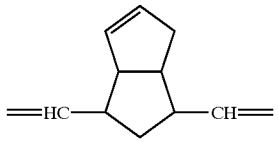

and represents a preferred subject of the invention. A further preferred subject of the invention comprises crosslinked copolymers having structural units of the formula

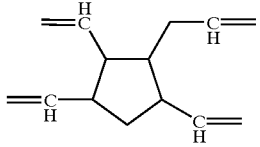

which can be prepared by the process of the invention.

The uncrosslinked or linear polymers comprise oligomers and polymers and can contain, for example, from 5 to 5000, advantageously from 10 to 2000, preferably from 20 to 1000, with particular preference from 20 to 500 and, with especial preference, from 20 to 300 structural units. Where the polymers are processed further preference is given to relatively low molecular weights, and in the case of processing to mouldings use is judiciously made of polymers having relatively high molecular weights.

Depending on the nature and amount of the monomers used, the polymers of the invention may have different properties. Some are notable for very high oxygen permeability, excellent dielectric properties (low dielectric constants, low loss factors or tan δ values), good thermal stability (glass transition temperatures above 100° C.), good toughnesses (impact and notched impact strength), flexibility and mechanical strengths (fracture resistance), hardness and low water absorption. Others have outstanding optical properties, such as high transparency and low reflective indices, for example. Also deserving of emphasis are the low shrinkage and the excellent surface properties (smoothness, gloss, adhesion). They can therefore be used in a very wide variety of industrial fields.

As coats on the surface of carrier materials, the polymers of the invention are notable for high adhesive strength. In addition, the coated materials are notable for high surface smoothness and gloss. Among the good mechanical properties particular emphasis should be placed on the low shrinkage and high impact strength, but also the thermal stability. Also deserving of mention are the ease of demoulding and the high solvent resistance. The surfaces can be modified further, for example painted or printed, and the high adhesive strengths of the coatings should be mentioned in this case, too.

The polymers obtainable in accordance with the invention are particularly suitable for producing articles of all kinds, such as mouldings for cars, boats, leisure articles, pallets, pipes, sheets, etc.; as insulating materials for producing electrical and electronic components; as implants; as binders for coating materials; as heat-curable compositions for modelling or as adhesives for bonding substrates having low surface energies (Teflon®, polyethylene or polypropylene). The compositions of the invention can also be used to prepare coatings by thermal polymerization, it being possible to use both clear (transparent) and even pigmented compositions. Both white and colour pigments can be used. The production of mouldings by thermoplastic staping processes for consumer articles of all kinds should also be mentioned.

The compositions of the invention are also suitable in particular for producing protective coats. The invention also provides a variant of the process of the invention for producing coated materials, in which the composition of the invention is applied with or without solvent as a film to a carrier, for example by dipping, brushing, flow coating, rolling, knife coating or spin coating techniques, the solvent (if used) is removed, and the film is heated for polymerization. With this process it is possible to modify or protect the surfaces of substrates (corrosion protection).

The present invention provides, furthermore, a coated carrier material wherein a coat of the polymer of the invention has been applied to a substrate.

The present invention likewise provides a coated substrate having a cured film of the polymer of the invention.

Examples of suitable substrates (carrier materials) are those of glass, minerals, ceramics, plastics, wood, semimetals, metals, metal oxides and metal nitrides. The film thicknesses depend essentially on the desired use and can, for example, be from 0.1 to 1000 $\mu$m, preferably from 0.5 to 500 $\mu$m and, with particular preference, from 1 to 100 $\mu$m. The coated materials are notable for high adhesive strength and good thermal and mechanical properties.

The coated materials of the invention can be prepared by known methods such as brushing, knife coating, flow coating methods such as curtain coating or spin coating.

In the case of coatings, particularly good results are often achieved if the thermal metathesis polymerization is carried out with the additional use of cycloolefins which In addition contain from 1 to three, and preferably one, further double bonds and which in the context of the invention are polycyclic fused ring systems.

The examples which follow illustrate the invention. The names of the products IRGANOX, IRGAFOS, TINUVIN and CHIMASSORB are Registered Trademarks (®).

A) PREPARING THE CATALYSTS

EXAMPLE 1

Preparing

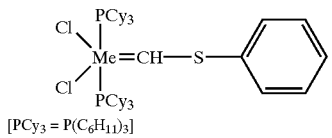

[PCy₃ = P(C₆H₁₁)₃]

a) 200 mg of RuCl₂[P(C₆H₁₁)₃]₂(=CH—C₆H₅) are dissolved in 10 ml of methylene chloride. At room temperature (RT) 5 equivalents of phenyl vinyl sulfide are added. After 30 minutes of stirring at RT the reaction mixture is concentrated in vacuo and the residue is washed twice with hexane and dried in vacuo. The pure product is obtained in virtually quantitative yield.

b) Alternatively to a) this compound can be prepared by reacting a brown suspension containing 1.32 g (4.7 mmol) of RuCl₂(cis,cis-cyclooctadiene), 1.42 ml (9.4 mmol) of 1,8-diazabicyclo[5.4.0]undec-7-ene and 2.7 g of trioyclohexylphosphine in 60 ml of isopropanol. The suspension is stirred for one hour at 80° C. The clear red solution obtainable is cooled for one hour at −20° C. Following the addition of 9.4 ml of a 1-molar HCl solution in diethyl ether stirring is continued for 15 minutes. 1.0 ml of 1-hexyne and 1.3 ml of phenyl vinyl sulfide are added to the yellow suspension. Further working up is as in a).

$^1$H NMR (CDCl₃): 17.63 (s, 1, carbene-H); 7.3 (m, 5, S—C₆H₅); 2.63 (m, 6, H$_\alpha$—PCy₃); 2.0–1.5 (m, 60, PCy₃). $^{13}$C NMR: 280.6 (carbene-C). Elemental analysis: C: 60.40 (calc.), 60.66 (found); H: 8.49 (calc.), 8.72 (found); Cl: 8.29 (calc.), 8.05 (found); P: 7.25 (calc.), 7.20 (found).

EXAMPLE 2

Preparing

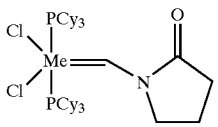

The pure product is obtained in virtually quantitative yield from 200 mg of RuCl₂[P(C₆H₁₁)₃]₂(=CH—C₆H₅) and 5 equivalents of N-vinyl-2-pyrrolidinone by the method of Example 1. $^1$H NMR (CDCl₃): 16.02 (s, 1, carbene-H).

EXAMPLE 3

Preparing

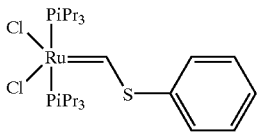

[PiPr₃ = P(C₃H₇)₃]

a) The pure product is obtained in virtually quantitative yield from 200 mg of RuCl₂[P(C₆H₁₁)₃]₂(=CH—C₆H₅) and 5 equivalents of phenyl vinyl sulfide by the method of Example 1.

b) Alternatively to a) this compound can be prepared by reacting a brown suspension containing 5.25 g (18.7 mmol) of RuCl₂(cis,cis-cyclooctadiene), 5.25 ml (37.4 mmol) of triethylamine and 7.5 ml of triisopropylphosphine in 250 ml of isopropanol. The suspension is stirred at 80° C. for three and a half hours. The clear red solution obtainable is cooled for one hour at −20° C. Following the addition of 37.5 ml of a 1-molar HCl solution in diethyl ether stirring is continued for 15 minutes. 1.0 ml of 1-pentyne and 4.9 ml of phenyl vinyl sulfide are added to the yellow suspension. Subsequent working up is as in Example 1a).

$^1$H NMR (CDCl₃): 17.65 (s, 1, carbene-H). $^{13}$C NMR (CDCl₃): 281.6 (carbene-C). $^{31}$P NMR (CDCl₃): 42.3. elemental analysis: C: 48.85 (calc.), 49.10 (found); H: 7.87 (calc.), 8.05 (found); Cl: 11.54 (calc.), 11.21 (found); P: 10.08 (calc.), 9.60 (found).

EXAMPLE 4

Preparing

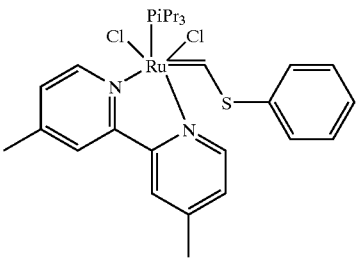

108 mg of RuCl₂(=CH—S—C₆H₅)[P(C₃H₇)₃]₂ are dissolved in in 15 ml of methylene chloride. 33 mg of 4,4'-dimethylbipyridine (1 equivalent) are added at room temperature. After 30 minutes of stirring at room temperature the reaction mixture is concentrated in vacuo and the residue is washed three times with 5 ml of hexane and dried in vacuo. The pure product is obtained in virtually quantitative yield. $^1$H NMR (CDCl₃): 19.11 (d, 1, $^3$J$_{PH}$=4,38 Hz, carbene-H).

B) USE EXAMPLE

EXAMPLE 5

5.1. Polymerizing DCPD (=dicyclopentadiene):

3 mg of catalyst are dissolved in 3 g of DCPD (from BFGoodrich, 98%) (0.1% by weight). Then the heat produced and the onset temperatures are measured by means of DSC (differential scanning calorimetry). In a second measurement the glass transition temperature of the poly-DCPD is measured.

| Catalyst | ΔH (J/g) | Onset (° C.) | T$_g$ (° C.) |
|---|---|---|---|
| RuCl₂(=CH—SC₆H₅)(PCy₃)₂ | 325 | 87 | 140 |
| RuCl₂(=CH—SC₆H₅)(PiPr₃)₂ | 349 | 80 | 152 |

5.2. Comparing the Polymerization of Cyclic Olefins:

1 mg of RuCl₂(=CH—SC₆H₅)(PiPr₃)₂ is dissolved in 3 g of liquid olefin (0.035% by weight).

Curing cycle: 1 hour at 120° C. and 2 hours at 150° C. The glass transition temperature is measured by means of DSC.

| Monomer | Manufacturer | $T_g$ (° C.) |
|---|---|---|
| Cyclohexenylnorbornene | Shell | 97 |
| DCPD | B. F. Goodrich | 127 |
| Flash 7T (DCPD/TCPD) | B. F. Goodrich | 139 |
| MTD | B. F. Goodrich | 152 |
| Multicyclic olefin oligomers | Shell | 97 |

5.3. Effect of Catalyst Concentration on the Glass Transition Temperature of Poly-DCPD:

A defined amount of $RuCl_2(=CH-SC_6H_5)(PCy_3)_2$ is dissolved in 3 g of DCPD.

Curing cycle: 1 hour at 120° C. and 2 hours at 150° C. The glass transition temperature is measured by means of DSC.

| Monomer | Manufacturer | Catalyst concentration (% by wt) | $T_g$ (° C.) |
|---|---|---|---|
| DCPD | B. F. Goodrich | 0.05 | 119 |
| DCPD | B. F. Goodrich | 0.1 | 140 |
| DCPD | Shell | 0.1 | 74 |
| DCPD | Shell | 0.2 | 116 |

EXAMPLE 6
Ring Closure Reaction of Diethyl 2-Diallylmalonate:

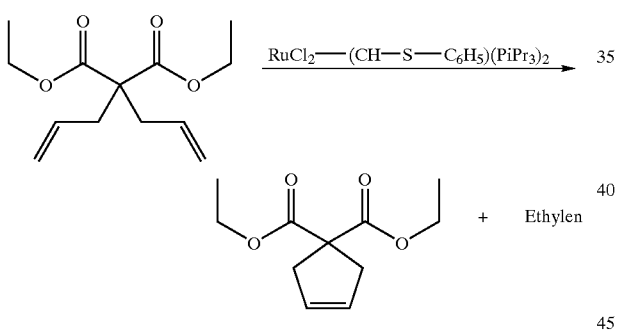

120 mg (0.5 mmol) of diethyl 2-diallylmalonate are dissolved in 2 ml of methylene chloride. The catalyst $RuCl_2(=CH-SC_6H_5)(PCy_3)_2$, 0.5 mol-% based on open-chain diolefin, is added under nitrogen. Reaction is allowed to take place at room temperature with stirring and the conversion, i.e. the formation of the cyclic olefin, is monitored by means of GC at periodic intervals of time.

| Example No. | Solvent | Temp. (° C.) | Time (h) | Conversion (%) |
|---|---|---|---|---|
| 6.1 | Methylene chloride | RT | 24 | 9 |
| 6.2 | 1,1,2-Trichloroethane | 80 | 1 | 15 |
| 6.3 | 1,1,2-Trichloroethane | 100 | 1 | 12 |

EXAMPLE 7
Effect of Additives [Antioxidants, HALS (HALS:Hindered Amine Light Stabilizers), UV absorbers]:

7.1. DCPD (98%, BFGoodrich) is admixed with 0.025% by weight of $[RuCl_2(=CHSPh)(PiPr_3)_2]$ and 1% by weight of the relevant additive. Curing conditions: 2 hours at 120° C., 1 hour at 150° C. Determination of $T_g$ by DSC.

| Additive | $T_g$ in ° C. |
|---|---|
| Control (no additive added) | 142 |
| 1 | 140 |
| 2 | 140 |
| 3 | 142 |
| 4 | 143 |
| 5 | 139 |
| 6 | 140 |
| 7 | 140 |
| 8 | 141 |
| 9 | 89 |
| 10 | 142 |
| 21 | 142 |
| 22 | 141 |
| 23 | 142 |
| 24 | rubberlike |
| 25 | rubberlike |
| 31 | rubberlike |
| 32 | 138 |
| Blend 1[a] | 138 |
| Blend 2[b] | 140 |

[a]Blend 1: 0.75% by weight of additive 8, 0.25% by weight of 12, 0.4% by weight of 21.
[b]Blend 2: 0.75% by weight of 8, 0.25% by weight of 12, 0.4% by weight of 21, 0.2% by weight of 32.

Antioxidants:

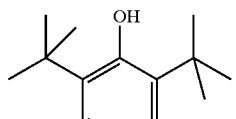

1

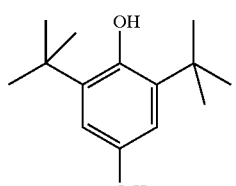

2

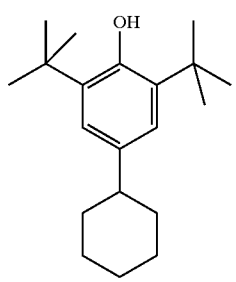

3

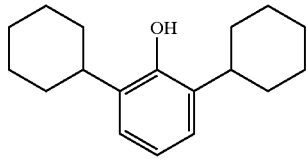

4

-continued

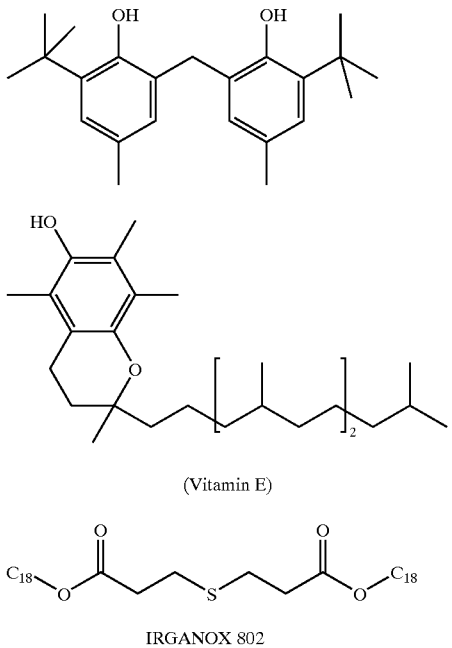

(Vitamin E)

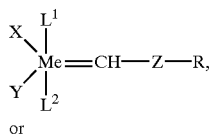

IRGANOX 802

What is claimed is:

1. A compound of the formula

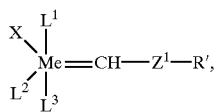
(Ia)

or

(Ib)

in which Me is ruthenium or osmium;

X, and Y independently of one another are anionic ligands or X and Y together are bisanionic ligands;

$L^1$, $L^2$ and $L^3$ independently of one another are monodentate, neutral $e^-$ donor ligands, with the proviso that one or two ligands from the group $L^1$, $L^2$ and $L^3$ are tertiary-substituted phosphine ligands selected from the group consisting of $(i\text{-}C_3H_7)_3P$, $(sec\text{-}C_4H_9)_3P$, $(C_5H_9)_3P$ and $(C_6H_{11})_3P$;

Z is sulfur or the group

(A′)

or

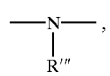
(A)

in which R′″ is hydrogen or a hydrocarbon radical;

$Z^1$ is oxygen, sulfur or a group

(A)

or A′;

R is unsubstituted or substituted aryl if Z is sulfur or is a hydrocarbon radical if Z is a group A or A′; and R′ is a hydrocarbon radical, or an isomer of this compound;

with the exception of compounds (Ib), wherein one of $L^1$, $L^2$ and $L^3$ represents carbonyl.

2. A compound of the formula Ia–Ib according to claim 1, wherein the ligands from the group $L^1$, $L^2$ and $L^3$ are monodentate, neutral $e^-$ donor ligands having electron donor properties, two ligands from this group together are bidentate, neutral $e^-$ donor ligands and derived from unsubstituted or substituted heteroarenes selected from the group consisting of furan, thiophene, pyrrole, pyridine, bis-pyridine, picolylimine, γ-pyran, γ-thiopyran, phenanthroline, pyrimidine, bis-pyrimidine, pyrazine, indole, coumarone, thionaphthene, carbazole, dibenzofuran, dibenzothiophene, pyrazole, imidazole, benzimidazole, oxazole, thiazole, bis-thiazole, isoxazole, isothiazole, quinoline, bis-quinoline, isoquinoline, bis-isoquinoline, acridine, chromene, phenazine, phenoxazine, phenothiazine, triazine, thianthrene, purine, bis-imidazole and bis-oxazole.

3. A compound of the formula Ia according to claim 1, wherein Z is sulfur and R is unsubstituted phenyl or phenyl which is substituted by one or more substituents from the group consisting of $C_1$–$C_6$alkyl, $C_1$–$C_6$alkoxy, carboxyl, $C_1$–$C_6$alkoxycarbonyl, $C_1$–$C_6$haloalkyl, nitro, sulfo, ammonium and halogen.

4. A compound of the formula

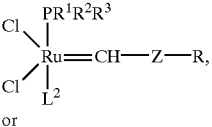
(I′a)

or

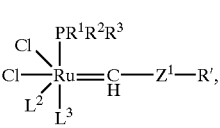
(Ib′)

according to claim 1 in which $L^2$ and $L^3$ independently of one another are monodentate, neutral $e^-$ donor ligands; $R^1$, $R^2$ and $R^3$ independently of one another are selected from the group consisting of $(i\text{-}C_3H_7)_3$, $(sec\text{-}C_4H_9)_3$, $(C_5H_9)_3$ and $(C_6H_{11})_3$;

Z is sulfur or the group

(A′)

or A, in which R′″ is hydrogen or a hydrocarbon radical selected from the group consisting of $C_1$–$C_{20}$alkyl, $C_3$–$C_8$-cycloalkyl, $C_3$–$C_8$heterocycloalkyl, $C_5$–$C_{12}$aryl, $C_1$–$C_9$heteroaryl and $C_6$–$C_{13}$aralkyl, which alkyl, cycloalkyl, heterocycloalkyl, aryl and heteroaryl are unsubstituted or substituted by $C_1$–$C_6$alkyl, $C_1$–$C_6$haloalkyl, $C_1$–$C_6$alkoxy, carboxyl, $C_1$–$C_6$alkoxycarbonyl, $C_5$–$C_{12}$aryl, $C_5$–$C_{12}$-aryloxy, —$NO_2$ or halo;

$Z^1$ is oxygen, sulfur or a group

 (A)

or A' with the definitions specified for R'";

R is unsubstituted or substituted aryl if Z is sulfur or is a hydrocarbon radical having the definitions specified for R'" if Z has the definition of the group A or A'; and R' is a hydrocarbon radical having the definitions specified for R'", or an isomer of this compound; with the exception of compounds (Ib), wherein one of $L^1$, $L^2$ and $L^3$ represents carbonyl.

5. A compound of the formula I'a–I'b according to claim 4, wherein $L^2$ and $L^3$ independently of one another are pyridyl which is unsubstituted or substituted by one or more substituents selected from the group $C_1$–$C_{12}$alkyl, $C_3$–$C_{11}$heterocycloalkyl, $C_1$–$C_9$heteroaryl, monoamino, diamino and —C(=O)H; or the two ligands $L^2$ and $L^3$ together are bis-pyridine, phenanthroline, bis-thiazole, bis-pyrimidine, bis-quinoline or picolylimine which are unsubstituted or substituted by one or more substituents selected from the group $C_1$–$C_{12}$-alkyl, $C_6$–$C_{10}$aryl and cyano, where the substituents alkyl and aryl are in turn unsubstituted or substituted by one or more substituents selected from the group $C_1$–$C_{12}$alkyl, nitro, monoamino, diamino and nitro- or diamino-substituted —N=N—$C_8$–$C_{10}$aryl;

$R^1$, $R^2$ and $R^3$ are isopropyl, sec-butyl, cyclopentyl or cyclohexyl;

Z is sulfur or a group A', in which R'" is hydrogen, $C_1$–$C_4$alkyl, phenyl or $C_1$–$C_4$-alkyl-substituted phenyl;

$Z^1$ is oxygen, sulfur or the group A or A' with the definitions specified for R'";

$R^1$ is phenyl if Z is sulfur or is $C_1$–$C_4$alkyl, phenyl or $C_1$–$C_4$alkyl-substituted phenyl if Z has the definition of the group A'; and R' is $C_1$–$C_4$alkyl, phenyl or $C_1$–$C_4$alkyl-substituted phenyl, or an isomer of this compound.

6. Dichlorobis[tricyclohexylphosphino] phenylthiomethinoruthenium or an isomer of this compound according to claim 1.

7. Dichlorobis[tricyclohexylphosphino]-1-(2-oxopyrrolidino)methinoruthenium or an isomer of this compound according to claim 1.

8. A composition comprising (α) dicyclopentadiene or another strained cycloolefin, or dicyclopentadiene in a mixture with another strained cycloolefin, and (β) a catalytic amount of at least one compound of the formulae Ia–Ib according to claim 1, in which Me is ruthenium or osmium and X, Y, $L^{1-}$, $L^2$, $L^3$, Z, $Z^1$, R and R' are as defined therein, and isomers of these compounds and, optionally, further additives for polymers.

9. A process for preparing metathesis polymers, which comprises heating a composition comprising (α') dicyclopentadiene or another strained cycloolefin, or dicyclopentadiene in a mixture with another strained cycloolefin, and (β') a catalytic amount of at least one compound of the formulae Ia–Ib according to claim 1, in which Me is ruthenium or osmium and X, Y, $L^1$, $L^2$, $L^3$, Z, $Z^1$, R and R' are as defined therein, and isomers of these compounds and, optionally, further additives for polymers and, optionally, subjecting the obtainable metathesis polymer to a shaping process.

10. A process for preparing metathesis polymers, which comprises heating a composition comprising (α') dicyclopentadiene or another strained cycloolefin, or dicyclopentadiene in a mixture with another strained cycloolefin, and (β') a catalytic amount of at least one compound of the formulae I'a–I'b according to claim 4, in which $L^2$, $L^3$, Z, $Z^1$, R, R', $R^1$, $R^2$ and $R^3$ are as defined therein, and isomers of these compounds and, optionally, further additives for polymers and, optionally, subjecting the obtainable metathesis polymer to a shaping process.

* * * * *